United States Patent [19]

Horner et al.

[11] 4,404,304

[45] Sep. 13, 1983

[54] CHROMAN DERIVATIVES USEFUL AS STABILIZERS FOR POLYPROPYLENE AND β-CAROTIN

[75] Inventors: Michael Horner, Neustadt; Dieter Horn, Heidelberg; Erik Lueddecke; Gernot Teege, both of Ludwigshafen, all of Fed. Rep. of Germany

[73] Assignee: BASF Aktiengesellschaft, Fed. Rep. of Germany

[21] Appl. No.: 344,191

[22] Filed: Jan. 28, 1982

[30] Foreign Application Priority Data

Feb. 4, 1981 [DE] Fed. Rep. of Germany ....... 3103707

[51] Int. Cl.³ .................... C07D 311/72; C08K 5/09
[52] U.S. Cl. ........................................ 524/110; 585/3; 549/408
[58] Field of Search ............... 260/345.5; 549/408; 585/3; 524/110

[56] References Cited

FOREIGN PATENT DOCUMENTS 1114319  4/1962  Fed. Rep. of Germany ...... 549/408
1139102 11/1962  Fed. Rep. of Germany ...... 549/408
3010505 10/1981  Fed. Rep. of Germany ...... 549/408

*Primary Examiner*—Nicky Chan
*Attorney, Agent, or Firm*—Keil & Witherspoon

[57] ABSTRACT

Novel chroman derivatives

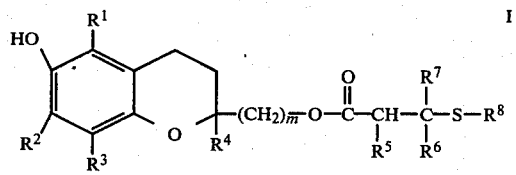

where $R^1$, $R^2$, $R^3$, $R^4$ and $R^5$ are each H or $C_1$–$C_4$-alkyl, $R^6$ and $R^7$ are each H, $C_1$–$C_4$-alkyl or aryl, m is 1, 2 or 3, and $R^8$ is alkyl or alkenyl of up to 30 carbon atoms, the preparation of these compounds, and their use as stabilizers for organic materials.

7 Claims, No Drawings

CHROMAN DERIVATIVES USEFUL AS STABILIZERS FOR POLYPROPYLENE AND β-CAROTIN

The present invention relates to novel chroman derivatives of the general formula I

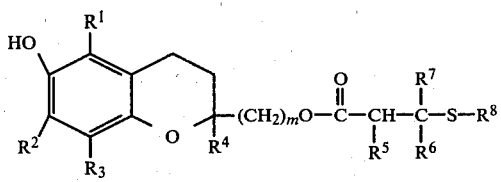

where $R^1$, $R^2$, $R^3$, $R^4$ and $R^5$ are each H or $C_1$-$C_4$-alkyl, $R^6$ and $R^7$ are each H, $C_1$-$C_4$-alkyl or aryl, m is 1, 2 or 3, and $R^8$ is alkyl or alkenyl of up to 30 carbon atoms.

The invention further relates to the preparation of the compounds I, to their use as light stabilizers, heat stabilizers and oxidation stabilizers for organic materials, especially for plastics, and to the organic materials stabilized with these compounds.

Compounds containing the structural unit

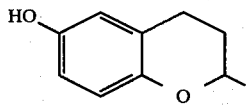

have been known for a long time as stabilizers for plastics and organic materials. The best known of these compounds, namely α-tocopherol (vitamin E)

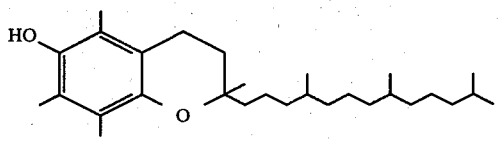

is an effective stabilizer for plastics, as disclosed in German Pat. Nos. 1,114,319 and 1,139,102. α-Tocopherol is, however, relatively difficult to prepare and is therefore, for most purposes, too expensive to use as a stabilizer. Furthermore, α-tocopherol frequently causes undesirable discoloration. From a processing point of view also, α-tocopherol, being an oily substance very prone to oxidation, presents problems.

It is an object of the present invention, as of the prior German Laid-Open Application DOS No. 3,010,505, to replace α-tocopherol by stabilizers which substantially have the same type of effect but are cheaper, and which produce similar or better results.

We have found that this object is achieved by the novel chroman derivatives I defined at the outset, which are exceptionally suitable for use as stabilizers for organic materials, including, in particular, plastics.

Further, we have found various processes for the preparation of the chroman derivatives I, which are described in detail below. Amongst the compounds I, those where $R^1$, $R^2$, $R^3$ and $R^4$ are methyl are preferred, since chroman derivatives having this structure are particularly easy to prepare. Compounds I where $R^1$, $R^2$, $R^3$ and $R^4$ are each radicals other than methyl are obtainable in a similar manner, and their action as stabilizers, according to our observations to date, is about the same as in the case of the tetramethylchroman derivatives.

An essential structure for achieving the stabilizing effect is the alkyl or alkenyl radical $R^8$ which, in accordance with the definition given, should be of 1 to 30, preferably 7 to 30, carbon atoms, linear radicals being preferred.

$R^5$, $R^6$ and $R^7$ are each preferably hydrogen or methyl, but, according to our observations to date, compounds containing other radicals exhibit similar stabilizing actions.

The compounds I are obtainable by conventional acid-catalyzed esterification of an alcohol II

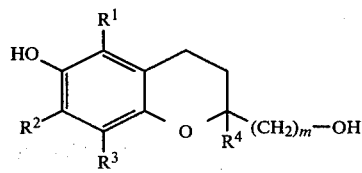

with a mercaptopropionic acid derivative III

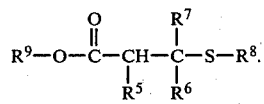

The preparation of the chroman derivatives II is described in the prior German Laid-Open Application DOS No. 3,010,504, and the starting compounds III are known from Houben-Weyl, Methoden der Organischen Chemie, Volume 9 (1955), page 124, or are obtainable in a conventional manner by the base-catalyzed addition reaction of a thiol VI with the appropriate acrylyl compound.

The details of the numerous embodiments of the esterification of the alcohols III ($R^9$=H) and of the trans-esterification of the esters III ($R^9$=$C_1$-$C_4$-alkyl), in respect of the acid used as the catalyst, the removal of the water of reaction, the temperature and the reaction time, are well known, so that detailed description is unnecessary here.

Another method for the preparation of I comprises the addition reaction of a thiol VI $$R^8SH \qquad VI$$

with a chroman derivative IV

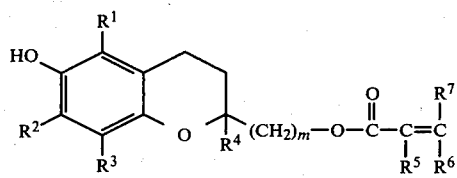

This reaction is also known per se, and is preferably carried out in a customary manner, in the presence of an inert solvent and of 0.1–10% by weight, based on IV, of a base.

Toluene, methylene chloride, ethylene chloride, tetrahydrofuran, diethyl ether and methyl tert.-butyl ether are suitable solvents.

Sodium and potassium hydroxide in powder form, sodium or potassium alcoholates, eg. sodium methylate or sodium ethylate, phenolates, eg. sodium phenolate, tertiary amines, eg. triethylamine, or basic ion exchangers are suitable bases.

The addition reaction is conventionally carried out at room temperature, but can also be carried out at up to about 100° C., particularly when $R^6$ and $R^7$ are alkyl or aryl. Working-up is carried out using conventional techniques and therefore requires no detailed description here.

The compounds IV can be prepared in a conventional manner by esterification of an alcohol II with an acrylic acid derivative VII

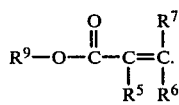   VII

Instead of the acrylic acid derivative IV, it is also possible to react the corresponding β-halopropionic acid derivative V

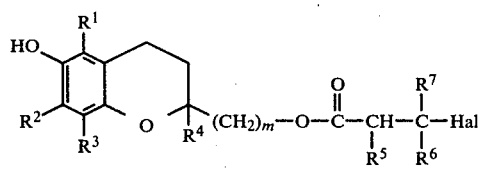   V where Hal is chlorine or bromine, with the thiol, although it is necessary to use an equimolar amount of the base in this case. The type of base, the type of solvent, the reaction temperature and the working-up are the same as in the case of the reaction of the acrylic acid derivative.

The compounds V, in turn, are obtainable by the esterification of II with a halopropionic acid derivative

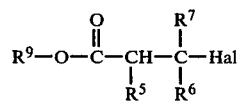

In all cases, a crystalline product I can be purified, if necessary at all, by recrystallization, for example from methanol/water. An oily product can be purified as follows: the product is dissolved in an inert solvent, the solution is shaken with an absorbent, eg. silica gel, to adsorb the product, the adsorbent is filtered off, the product is desorbed with fresh solvent, and the solvent is again stripped off. Examples of suitable solvents are diethyl ether, methyl tert.-butyl ether, toluene and methylene chloride.

The novel chroman derivatives I are outstandingly useful as heat stabilizers, light stabilizers and oxidation stabilizers for organic materials. Examples of relevant organic materials are fats, oils, waxes, pharmaceuticals and cosmetic formulations and especially plastics. Depending on the severity of the conditions to which these materials are exposed, the stabilizers are used in concentrations of from 0.005 to 1.0, as a rule from 0.01 to 0.5, % by weight, based on the amount of plastic. For very sensitive substrates, for example vitamins, the concentrations can be as high as 20% by weight. The novel stabilizers may be used alone or mixed with other stabilizers, in particular phenolic stabilizers, for example neopentyl glycol tetra-[3-(3,5-di-tert.-butyl-4-hydroxyphenyl)-propionate] or octadecyl 3-(3,5-di-tert.-butyl-4-hydroxyphenyl)-propionate.

The particular advantage of the novel stabilizers is that they substantially improve the processing stability and long-term stability of the above phenolic stabilizers, and are thus used as synergists for these commercial stabilizers. This effect can be used to effect a substantial reduction in the concentration of the commercial stabilizers, some of which are expensive, without the long-term stability being adversely affected. As a rule, the processing stability is even significantly improved. The synergistic stabilizer is in general employed in an amount of from 10 to 500% by weight, based on the amount of the novel chroman derivative I.

Further, the chroman derivatives I can be used in combination with other additives, eg. calcium stearate, which are in general employed in amounts of from 50 to 500% by weight, based on the amount of the derivative I. Using such combinations, only very slight discolorations and outstanding processing stability are obtained in plastics. In general, stabilizers serve to protect the organic materials against changes and decomposition, which in the case of plastics means, in the main, against degradation and undesirable crosslinking of the macromolecules, these being changes which manifest themselves as aging, embrittlement, discoloration and lowering of softening point.

The following criteria are particularly relevant in assessing the suitability and effectiveness of stabilizers:
1. Color The stabilizer should not discolor the substrate. This requirement, which is of course particularly important for colorless plastics, is satisfactorily or excellently met by the novel stabilizers in the case of most plastics; as a rule, the novel compounds are superior to conventional stabilizers, including α-tocopherol. The quantitative determination of the color characteristics can be carried out by various methods, for example by the yellowness test-ASTMD 1925.

2. Processing Stability

This refers to the degree to which the properties of thermoplastics remain constant when exposed to mechanical stresses and heat during molding processes, such as extrusion and injection-molding. In this respect, the novel stabilizers give particularly good results. A measure of the processing stability is the change in melt characteristics of the thermoplastic after repeated molding and remelting. The corresponding melt index test is described in DIN 53,735. Another important criterion of processing stability is constancy of color, which can be assessed by, for example, the yellowness test.

3. Long-term Stability

The behavior of plastics when exposed to severe thermal and oxidative conditions is an indication of the period for which the quality of the plastic will remain constant when the material is used for a particular application; this means that the data determined by the corresponding test (DIN 53,383, page 1) permit an estimate of the useful life of the plastic article. The novel stabilizers offer advantages in long-term stability when used in conjunction with synergistic agents.

Further details concerning tests of the quality of the novel stabilizers are to be found in the experiments on the effects of the stabilizers.

EXAMPLES OF THE PREPARATION OF THE CHROMAN DERIVATIVES I AND THEIR INTERMEDIATES

In the text below, A is the radical

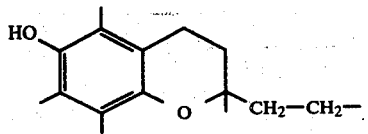

EXAMPLE 1

Preparation of A acrylate

A solution of 125 g (0.5 mole) of 6-hydroxy-2,5,7,8-tetramethyl-2-(2-hydroxyethyl)-chroman (A—OH), 258 g (3.0 moles) of methyl acrylate, 2 g of hydroquinone, 8 g of p-toluenesulfonic acid and 125 ml of toluene was heated in a distillation apparatus, and an azeotropic mixture of methyl acrylate and methanol (boiling range 68°–73° C.) was distilled off. After the end of the reaction, thin layer chromatography of a sample showed that the A—OH was completely converted. The excess methyl acrylate was stripped off in a spinning band column, and the residue was shaken with 160 g of silica gel (70–230 mesh) in a mixture of 360 ml of toluene and 40 ml of ethyl acetate. The adsorbent was filtered off and washed with 300 ml of the solvent mixture, and the filtrate was again freed from solvent. The A acrylate remained in the form of a yellowish oil which slowly crystallized. Yield: 85%.

EXAMPLE 2

Preparation of A methacrylate

The process was carried out as described in Example 1, except that 287 g (3.4 moles) of methyl methacrylate were used instead of the acrylate, and the A methacrylate was produced, in 91% yield, as an orange oil which slowly crystallized.

EXAMPLE 3

Preparation of A p-methoxycinnamate

A mixture of 20 g (0.08 mole) of A—OH, 14.3 g (0.08 mole) of p-methoxycinnamic acid, 1.5 g of p-toluenesulfonic acid and 800 ml of toluene was refluxed for 20 hours, and the water of reaction was removed continuously. The p-toluenesulfonic acid was separated off, the mixture was shaken twice with 250 ml of saturated sodium bicarbonate solution and with 250 ml of water, and the organic phase was dried over anhydrous $Na_2SO_4$ and concentrated to give the product. The latter was obtained in the form of colorless crystals of melting point 113°–114° C. (from methanol), in 96% yield.

EXAMPLE 4

A 3,3-dimethylacrylate

The process was carried out as described in Example 3, except that 6.4 g (0.08 mole) of 3,3-dimethylacrylic acid were used instead of the p-methoxycinnamic acid, and the A 3,3-dimethylacrylate was obtained in 81% yield, as a brownish oil.

EXAMPLES 5 TO 10

Preparation of β-mercaptopropionic acid derivatives from the acrylic acid derivatives A solution of 0.05 mole of the A acrylic acid derivative in 40 ml of anhydrous tetrahydrofuran was added, in the course of 10 minutes, to a solution of 0.05 mole of a thiol $R^8SH$, 0.1 g of sodium methylate and 30 ml of anhydrous tetrahydrofuran, and the mixture was stirred for 15 hours at 25° C. and then extracted in a conventional manner with ether. Further working up gave the products I in the yields indicated in Table 1.

TABLE 1

Chroman derivatives I: $AO-\overset{O}{\underset{\|}{C}}-\overset{R^5}{\underset{|}{CH}}-\overset{R^7}{\underset{|}{C}}-S-R^8$
$\qquad\qquad\qquad\qquad\qquad\quad R^5\ \ R^6$

| Example No. | $AO-\overset{O}{\underset{\|}{C}}-\overset{R^5}{\underset{\|}{C}}=\begin{matrix}R^6\\ R^7\end{matrix}$ | $R^8$—SH $R^8$ | Chroman derivative I Melting point | Yield |
|---|---|---|---|---|
| 5 | $R^5 = R^6 = R^7 = H$ | -n-butyl | oil[a] | 80% |
| 6 | $R^5 = R^6 = R^7 = H$ | n-octyl | oil[ab] | 85% |
| 7 | $R^5 = R^6 = R^7 = H$ | n-dodecyl | oil[ab] | 97% |
| 8 | $R^5 = CH_3$; $R^6 = R^7 = H$ | n-dodecyl | oil[ab] | 83% |
| 9 | $R^5 = H$; $R^6 = R^7 = CH_3$ | n-dodecyl | oil[b] | 32% |
| 10 | $R^5 = R^6 = H$ $R^7$ = p-methoxyphenyl | n-dodecyl | oil[b] | 15% |

[a] crystallizing slowly
[b] purified over silica gel

EXAMPLE 11

Preparation of a chroman derivative I from A—OH and III 25 g (0.1 mole) of A—OH, 25.6 g (0.1 mole) of methyl 4-thiapalmitate, 0.7 g of p-toluenesulfonic acid and 300 ml of toluene were refluxed for 3 hours in a distillation apparatus, and the methanol produced was distilled off. Conventional working-up gave the compound I, where $R^5$, $R^6$ and $R^7$ were each H and $R^8$ was n-dodecyl, in the form of a slowly crystallizing, brownish oil, in 85% yield.

This compound was prepared from A—OH and the free 4-thiapalmitic acid in a similar manner. In this case the yield was 80%.

Experiments on the stabilizing action of the chroman derivatives I

1. Color of polypropylene

The color quality was measured in terms of the yellowness index (YI), by the yellowness test (ASTMD 1925).

The test material used was additive-free dechlorinated polypropylene; in each case the stabilizer was incorporated into the polypropylene in the same manner, and the material was then molded into granules of 15 mm layer thickness. The YI values quoted are each the mean of two measurements. The higher these values, the lower the color quality. The results are shown in Table 2. The values roughly correspond to the following (visually) perceptible discolorations of the test material:

2 no discernible discoloration 3-5 very slight discoloration
5-10 slight but distinctly discernible discoloration
10-20 marked discoloration
20 severe discoloration.

2. Processing stability of polypropylene

The polypropylene samples (the material used being the same as for the color test) were subjected to six extrusion and granulation sequences. The quotient $MFI_6/MFI_1$ was calculated from the melt indices (MFI) (for method of determination, see DIN 53,735) after the first and sixth extrusions. The higher this quotient, the lower the processing stability. The color measurements correspond to those in the color test. The results are shown in Table 3.

3. Oven Aging

Polypropylene sheets of 1 mm layer thickness were subjected to oven aging, as described in DIN 53,383, page 1, by heating the sheets in an oven, with access of fresh air, at 140° C. until they showed noticeable embrittlement. The visual test was carried out every 24 hours, ie. the aging time was measured in days. The lower the values, the lower the long-term stability. The values are mean values of ten measurements, and each have a deviation of up to about 5%. The results are summarized in Table 4.

TABLE 2

Yellowness index YI of polypropylene granules

| Experiment No. | Stabilizer | From Example | Amount % by weight | YI Index |
|---|---|---|---|---|
| | comparative | | | |
| 1 | without stabilizer | — | 0.1 | 1 |
| 2 | Q[x] | — | 0.1 | 8 |
| 3 | α-tocopherol | — | 0.1 | 18 |
| 4 | Q | — | 0.1 | 4 |
| | calcium stearate | | 0.2 | |
| 5 | α-tocopherol | — | 0.1 | 15 |
| | calcium stearate | | 0.2 | |
| | DSDP[xx] | | 0.2 | |
| 6 | α-tocopherol | — | 0.1 | 16 |
| | Q | | 0.05 | |
| | according to the invention | | | |
| | A—O—CO—CH$_2$—CH$_2$—S—R$^8$ | | | |
| 7 | R$^8$ = n-butyl | 5 | 0.1 | 16 |
| 8 | R$^8$ = n-octyl | 6 | 0.1 | 12 |

TABLE 2-continued

Yellowness index YI of polypropylene granules

| Experiment No. | Stabilizer | From Example | Amount % by weight | YI Index |
|---|---|---|---|---|
| 9 | R$^8$ = n-dodecyl | 7 | 0.1 | 10 |
| 10 | R$^8$ = n-dodecyl | 7 | 0.05 | 10 |
| | Q | | 0.05 | |

[x]Pentaerythrityl tetrakis-[3-(3,5-di-tert.-butyl-4-hydroxyphenol)-propionate]
[xx]Distearyl thiodipropionate

TABLE 3

Melt index quotient $MFI_6/MFI_1$ and yellowness index of polypropylene

| Experiment No. | Stabilizer | from Example | Amount % by weight | $MFI_6/MFI_1$ | YI ($YI_6 - YI_1$) |
|---|---|---|---|---|---|
| | comparative | | | | |
| 11 | without stabilizer | — | 0.1 | 7.3 | 4 |
| 12 | Q[x] | — | 0.1 | 2.5 | 13 |
| 13 | α-tocopherol | — | 0.1 | 1.9 | 10 |
| 14 | Q | — | 0.1 | 2.9 | — |
| | calcium stearate | — | 0.2 | | |
| 15 | α-tocopherol | — | 0.1 | 1.5 | 6 |
| | calcium stearate | — | 0.2 | | |
| | DSDP[xx] | — | 0.2 | | |
| 16 | α-tocopherol | — | 0.1 | 1.5 | 11 |
| | Q | — | 0.05 | | |
| | according to the invention | | | | |
| | A—O—CO—CH$_2$—CH$_2$—S—R$^8$ | | | | |
| 17 | R$^8$ = n-butyl | 5 | 0.1 | 1.5 | 10 |
| 18 | R$^8$ = n-octyl | 6 | 0.1 | 1.3 | 7 |
| 19 | R$^8$ = n-dodecyl | 7 | 0.1 | 1.3 | 5 |
| 20 | R$^8$ = n-dodecyl | 8 | 0.05 | 1.2 | 5 |
| | Q | | 0.05 | | |

[x],[xx]cf. footnotes to Table 2

TABLE 4

Oven-aging of polypropylene at 140° C.

| Experiment No. | Stabilizer | from Example | Amount % by weight | Aging time (hours) |
|---|---|---|---|---|
| | comparative | | | |
| 1 | without stabilizer | — | — | 24 |
| 2 | Q[x] | — | 0.1 | 707 |
| 3 | α-tocopherol | — | 0.1 | 70 |
| 4 | Q | — | 0.1 | 734 |
| | calcium stearate | — | 0.2 | |
| 5 | α-tocopherol | — | 0.1 | 329 |
| | calcium stearate | | 0.2 | |
| | DSDP[xx] | — | 0.2 | |
| 6 | α-tocopherol | — | 0.1 | 215 |
| | Q | — | 0.05 | |
| | according to the invention | | | |
| | A—O—CO—CH$_2$—CH$_2$—S—R$^8$ | | | |
| 27 | R$^8$ = n-butyl | 5 | 0.1 | 215 |
| 28 | R$^8$ = n-octyl | 6 | 0.1 | 340 |
| 29 | R$^8$ = n-dodecyl | 7 | 0.1 | 315 |
| 30 | R$^8$ = n-dodecyl | 8 | 0.05 | 655 |
| | Q | | 0.05 | |

[x],[xx]cf. footnotes to Table 2

4. Stability of β-carotin 4.1 Light stability 10 mg portions of a dry powder which consisted of 88.5 percent by weight of polyvinylpyrrolidone, 10% by weight of β-carotin and 1.5% by weight of a stabilizer were dissolved in 10 ml of air-saturated water. The intense yellow color of the clear solution corresponded to a light absorption maximum of 430 nm. At this wavelength, the extinction of a 1 cm layer of the solution was 0.8, and this was taken, for reference purposes, as 100%.

To determine the stability of the β-carotin to light, the solution was exposed to monochromatic UV light from a mercury high pressure lamp (365 nm; 1 mW/cm$^2$). The decoloration of the solution, ie. the decrease in extinction, is a measure of the destruction of the β-carotin, by the above irradiation. Table 5 shows the time in minutes required for the extinction to fall to 1/e-th, ie. to about 40%.

4.2 Shelf life

The β-carotin dry powder of the above composition was stored for seven days in the dark at 25° C. The extinction in percent of the original value $E_o(=100\%)$ was then determined. Solutions of 50 mg of the dry powder in 100 ml of chloroform were used for the measurements. The results of this test are also shown in Table 5.

TABLE 5

| Experiment No. | Stabilizer | from Example | Photo-stability min. | Shelf life, % of E |
|---|---|---|---|---|
| | comparative | | | |
| 1 | without stabilizer | — | 5 | 10 |
| 2 | α-tocopherol | — | 75 | 31 |
| 3 | ascorbyl palmitate | — | 22 | 20 |
| 4 | 2,6-di-tert.-butyl-4-methylphenol | — | 80 | 30 |
| | according to the invention | | | |
| 5 | A—O—CO—CH$_2$—CH$_2$—S—n-dodecyl | 8 | 92 | 40 |

We claim:

1. A chroman derivative of the general formula I

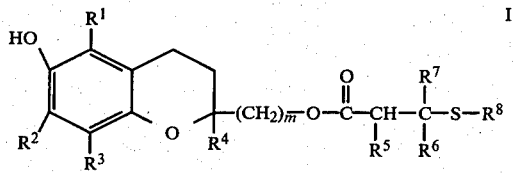

where $R^1$, $R^2$, $R^3$, $R^4$ and $R^5$ are each H or $C_1$–$C_4$-alkyl, $R^6$ and $R^7$ are each H, $C_1$–$C_4$-alkyl or aryl, m is 1, 2 or 3, and $R^8$ is $C_1$–$C_{30}$-alkyl or alkenyl of up to 30 carbon atoms.

2. A chroman derivative as claimed in claim 1, where $R^1$, $R^2$, $R^3$ and $R^4$ are each methyl, $R^5$, $R^6$ and $R^7$ are each hydrogen, and m is 2.

3. A method of stabilizing polypropylene and beta-carotin from the detrimental effects of light, heat and oxidizing agents which comprises: adding to said materials a stabilizing amount of a chroman derivative I as defined in claim 1.

4. A method of stabilizing polypropylene from the detrimental effects of light, heat and oxidizing agents which comprises adding to said polypropylene from 0.01 to 1.0% by weight, based on the weight of the polypropylene of a chroman derivative I as defined in claim 1.

5. A method of stabilizing beta-carotin from the effect of light, heat and/or oxidizing agents which comprises adding to said beta-carotin from 0.01 to 20% by weight, based on the weight of the beta-carotin of a chroman derivative as defined in claim 1.

6. A composition comprising an beta-carotin and, as a stabilizer, from 0.01 to 20% by weight of a chroman derivative I as defined in claim 1.

7. A composition as set forth in claim 6 which further contains from 50 to 500% by weight, based on the chroman derivative I of a second stabilizing agent.

* * * * *